United States Patent [19]

Thompson et al.

[11] Patent Number: 4,991,915
[45] Date of Patent: Feb. 12, 1991

[54] MICROWAVE MOISTURE SENSING ARRANGEMENT

[75] Inventors: Frank Thompson, Dale Road, Marple Stockport SK 6 6EZ, United Kingdom; John R. P. Clarke, Stockport, United Kingdom

[73] Assignees: Imperial Chemical Industries PLC Manchester Polytechnic, London; Frank Thompson, Stockport, both of England

[21] Appl. No.: 384,961

[22] Filed: Jul. 25, 1989

[30] Foreign Application Priority Data

Aug. 4, 1988 [GB] United Kingdom ............... 881851.9

[51] Int. Cl.$^5$ .............................................. G01N 22/04
[52] U.S. Cl. ................................. 324/640; 73/73; 73/336.5; 324/632
[58] Field of Search ................. 73/73, 336.5; 324/640, 324/632, 643

[56] References Cited

U.S. PATENT DOCUMENTS

| 3,079,551 | 2/1963 | Walker | 324/640 |
|---|---|---|---|
| 3,079,552 | 2/1963 | Walker | 324/640 |
| 3,441,844 | 4/1969 | Busker et al. | 324/640 |
| 3,693,079 | 9/1972 | Walker | 324/640 |
| 3,815,019 | 6/1974 | Wiles | 324/640 |
| 3,936,765 | 2/1976 | Lewis et al. | 331/1 R |
| 4,104,584 | 8/1978 | Miyai et al. | 324/632 |
| 4,131,845 | 12/1978 | Pakulis | 324/640 |
| 4,319,185 | 3/1982 | Hill | 324/640 |
| 4,361,801 | 11/1982 | Meyer et al. | 324/640 |
| 4,520,308 | 5/1985 | Rohde et al. | 324/632 |
| 4,546,311 | 10/1985 | Knöchel | 324/643 |
| 4,675,595 | 6/1987 | Hane | 324/640 |
| 4,727,311 | 2/1988 | Walker | 324/640 |
| 4,755,743 | 7/1988 | Jakkula | 324/643 |
| 4,788,853 | 12/1988 | Bell | 73/73 |
| 4,829,233 | 5/1989 | Flemming et al. | 324/632 |

FOREIGN PATENT DOCUMENTS 2129944  5/1984  United Kingdom ................ 73/73

OTHER PUBLICATIONS

Kent, M. et al., "Compact Microstrip Sensor for High Moisture Content Materials" J. Microwave Power, vol. 14, No. 4, pp. 363-365 (1979).

Primary Examiner—William A. Cuchlinski, Jr.
Assistant Examiner—Diego F. F. Gutierrez
Attorney, Agent, or Firm—Charles E. Baxley

[57] ABSTRACT

A microwave moisture sensing arrangement comprises an oscillator and a detector and a microwave strip line sensor connected between the two. The sensor is inserted into bulk, penetrable materials. The detector detects a change in received signal due to absorption of radiation from the sensor. Moisture content of the material is determined by calibration.

7 Claims, 1 Drawing Sheet

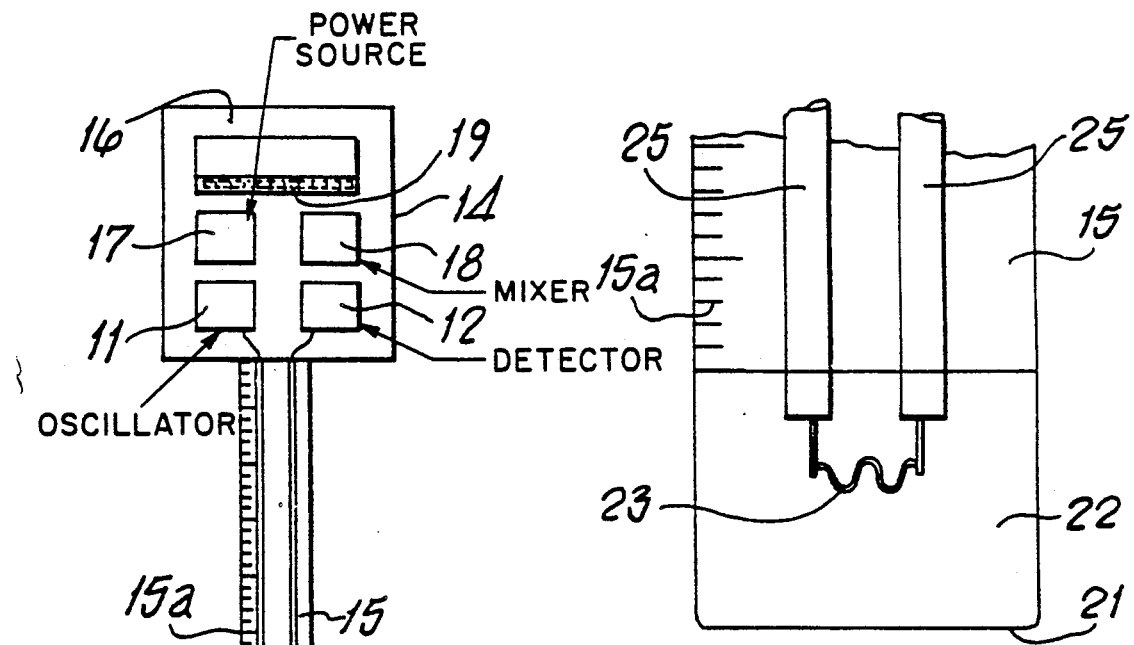
FIG.1
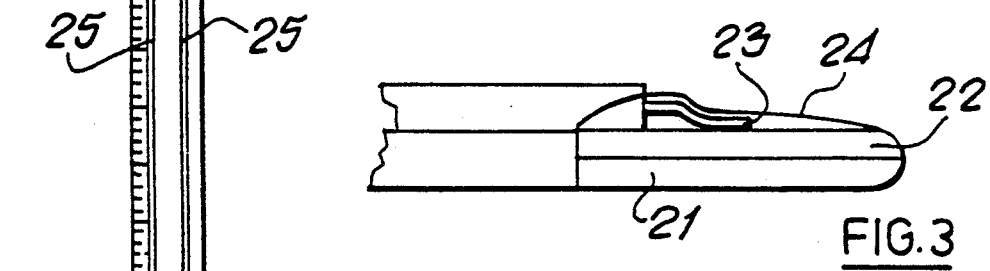
FIG.2
FIG.3
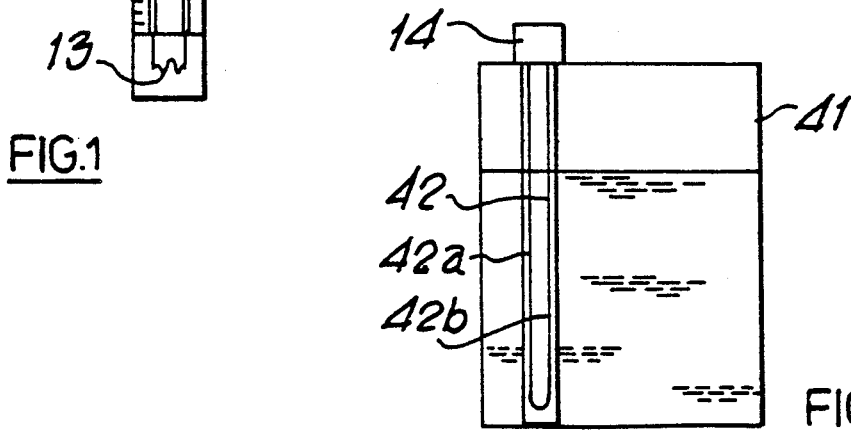
FIG.4

MICROWAVE MOISTURE SENSING ARRANGEMENT

BACKGROUND TO THE INVENTION

This invention relates to microwave moisture sensing arrangements.

In Y. Miyai "A New Microwave Moisture Meter for Grains", J. Microwave Power 13(2), 1978 is described a microwave moisture meter for grains using a hybrid microwave integrated circuit (MIC) and a strip line sensor which measures the microwave attenuation due to the measure of the moisture content of grain passing over the sensor.

The Miyai instrument is comprised in a casing adapted for installation in a window made in the wall of a hot-air dryer in which rice grains are circulated on a conveyor. A sensor plate incorporating the strip line sensor is on one wall of the casing and is placed against the window so that the rice grains flow over it.

Such an arrangement is useful only where flowing materials are being monitored, and was devised in particular for automatic operation of the rice-grain drying process.

There are many instances, however, where moisture content in static, penetrable materials needs to be measured. The Miyai instrument is quite unsuited to such measurements.

The present invention provides a microwave moisture sensing arrangement which is especially adapted to such measurements and is useful in a wide variety of circumstances and for measuring moisture in a wide variety of materials as well as being adapted for use as a level sensor.

SUMMARY OF THE INVENTION

The invention comprises a microwave moisture sensing arrangement comprising an oscillator and a detector and a microwave line sensor connected between said oscillator and said detector and adapted for insertion of said line sensor into bulk, penetrable materials whereby the detector detects a change in received signal.

The line sensor may be a strip line sensor as taught by Miyai or a coplanar transmission line. A coplanar transmission line comprises a pair of ground planes adjacent to the carrier on either side. An advantage of this form of transmission line is that all of the conductive material, including the ground plane material, can be arranged on the side of the carrying insulator remote from the sample.

The oscillator and detector may be contained in a housing and the line sensor carried on a probe projecting from said housing.

The line sensor may be connected to the oscillator and detector by waveguide means or coaxial link.

The said detector may detect attenuation of microwave signals through said sensor and/or phase change of such signals, and may comprise a microwave mixer, which may be a balanced mixer.

One of the problems of microwave moisture measurement, which is observed by Miyai but not dealt with in the construction of his meter, is that the change in microwave signal is affected by the density as well as the moisture content of the material under observation.

This density and moisture content affect is dealt with in the present instance by detecting phase change, which is affected by density differently to attenuation. Phase change is now detectable within the scope of a portable, inexpensive microwave moisture meter by using a microwave mixer, particularly a double balanced mixer such as is available from Plessey Microwave Ltd of Towcester, Northants, NN12 NJS, England.

Clearly the density in a bulk container of grain, for example, will depend upon the depth in the container as well as on the extent to which the load has settled due to vibration e.g. from transportation. Measurements of moisture content will be affected by such density variations and also by any local packing or loosening occasioned by the insertion of a probe, and this will lead to spurious results.

The facility to measure both attenuation and phase change, however, is not required for some measurements. The line sensor for example might be mounted on the end of a graduated probe adapted for insertion into a tank containing layers of different penetrable materials to detect the interface level or levels by observing the change in signal as the sensor passes between the layers. Such an arrangement can of course be used to check the homogeneity of a mixture of materials, settlement out of suspensions or of immiscible liquids and so on.

A line sensor comprises essentially a conductive plate with a dielectric substrate carrying a thin (e.g. printed) strip of conductor. The conductor may be e.g. copper or gold. The line may have a configuration other than a straight line, for example, it may have wavy or convoluted configuration, to increase the length of line in a given area or to produce a radiation field of a particular shape adapted to a specific measurement. It may be desired, for example, in level sensing applications, to have a small, sharply-defined field to increase the accuracy with which a level can be located. It may, on the other hand, be desired to have a uniform, extended field in order to integrate the attenuation or phase change effect over a region to get an average reading in a not necessarily homogeneous material. In general, the longer the line, the more sensitive will be the measurement since the attenuation will depend on the line length, but this, too, is moderated by line configuration.

A tank level sensor according to the invention may comprise an elongate loop line sensor depending into the tank from a unit containing the MIC and detector, the analogue attenuation signal varying with the level of liquid or moist material in the tank. Such an arrangement may have a uniformly constructed loop to give a linear attenuation/depth relationship. However, even a non-linear arrangement can be calibrated.

Another tank level sensor according to the invention, however, may have a small sensor drivable up and down the tank, possibly in a servo arrangement detecting only a sharp change in attenuation and/or phase and the level of such sharp change being determined from the position of the sensor.

BRIEF DESCRIPTION OF THE DRAWINGS

Embodiments of microwave moisture sensing arrangements according to the invention will now be described with reference to the accompanying drawings in which:

FIG. 1 is an elevation of a hand-held moisture sensing arrangement;

FIG. 2 is a view of a microwave strip line sensor head arrangement suitable for use with the arrangement illustrated in FIG. 1;

FIG. 3 is a cross section of the head of FIG. 2; and

FIG. 4 is a section through a liquid-storage tank having one kind of arrangement according to the invention used as a level sensor.

DETAILED DISCLOSURE OF THE PREFERRED EMBODIMENTS

The drawings illustrate microwave moisture sensing arrangements.

FIG. 1 illustrates such an arrangement comprising an oscillator 11 and a detector 12 and a microwave line sensor 13 connected between said oscillator and adapted for insertion of said line sensor into bulk, penetrable materials, whereby the detector 12 detects a change of received signal due to absorption by the material of radiation from the sensor.

The oscillator 11, which may comprise a hybrid microwave integrated circuit (MIC) as described by Miyai, or a Gunn diode or FET oscillator arrangement as from a domestic burglar alarm and the detector 12 (which may comprise for example a crystal or low-cost satellite dish amplifier or LNB) are contained in a housing 14, while the line sensor 13 is carried on a probe 15, which carries a graduation 15a in centimeters for example, projecting from the said housing 14. The graduations indicate the level of the uppermost layer when the sensor passes between the layers. Conversely, the graduations indicate how far below the uppermost layer the probe has penetrated when the signal changes.

The line sensor is shown in greater detail in FIGS. 2 and 3. It comprises a ground plate 21 e.g. of copper or gold with substrate 22 of dielectric such as fluor-glass or ferrite, with a printed-on strip 23 of copper or gold. The line 23 is covered with a protective film 24, which is, however, thin so as not substantially to reduce the field propagated by the strip line.

In FIG. 2, the line 23 is shown as a wavy line, which increases the propagated field, as would even more a convoluted or labryrinthine configuration, within a given spatial compass, thereby increasing the microwave power available for absorption by the moisture and hence the sensitivity of the arrangement.

The line 23 is connected to the oscillator 11 and the detector 12 by waveguide or other transmission line means 25.

The housing 14 has a handle 16 and includes a power source 17 and a double balanced microwave mixer 18 of the type sold by Plessey Microwave Limited aforementioned, used as a phase detector.

Analogue signals representative of attenuation and phase change can be digitised and displayed on a convenient display e.g. an LCD panel 19.

For a general purpose portable probe, it will suffice to give "raw" values of attenuation and/or phase change so that the arrangement can be calibrated for any particular function. If the arrangement is to be used for example with textile fibres, a series of measurements can be made using fibres with different known values of moisture regain, or different values measured by conventional means as by drying and weighting. The values of attenuation and/or phase change for a particular instrument corresponding to these known or conventionally measured values are then noted, so that when these values are observed in a sample for evaluation of moisture content, the look-up table can be consulted to find the actual moisture content.

Where the same probe is then to be used with a different material, it can be calibrated again and a new look-up table generated.

Usually, linear relationships can be assumed for interpolation purposes.

Where an arrangement is dedicated to a single end use, a microprocessor can convert the raw attenuation and phase change data into units representative of moisture content or level appropriate to the circumstances.

FIG. 4 illustrates such a dedicated arrangement for measuring water level in a tank 41 in which the housing 14 is located atop the tank and the line sensor comprises an elongate loop 42 with parallel, closely spaced sides 42a, 42b extending from near the housing 14 to the bottom of the tank 41.

The measurement of attenuation alone will usually provide a sufficiently good value of tank contents when the tank contains liquid water, but when the tank contents comprise sand or grain, a combination of attenuation and phase measurement by means well known in the art, is likely to give improved accuracy taking density into account.

Where, of course, strip line sensor is described and illustrated, it will be understood that coplanar sensor can be substituted.

We claim:

1. A microwave sensing arrangement comprising an oscillator and a detector and a microwave strip line sensor connected between said oscillator and said detector, said strip line sensor being insertable to a substantial depth into a static, bulk, penetrable material whereby the detector detects a change in received signal due to absorption by the material of radiation from the sensor, said oscillator and said detector being contained in a housing and said sensor being carried on a probe projecting from said housing a sufficient distance to permit said strip line sensor to be completely immersed in the material while leaving said housing outside the material.

2. An arrangement according to claim 1, in which the strip line sensor is connected to the oscillator and detector by transmission line means.

3. An arrangement according to claim 2, in which said transmission line means are waveguide means.

4. An arrangement according to claim 1, in which said detector detects attenuation of microwave signals through said sensor.

5. An arrangment according to claim 1, in which said detector detects phase change of microwave signals through said sensor.

6. An arrangement according to claim 5, in which said detector comprises a microwave mixer.

7. An arrangement according to claim 6, in which said microwave mixer comprises a double balanced mixer.

* * * * *